(12) United States Patent
Nabutovsky et al.

(10) Patent No.: US 8,170,664 B1
(45) Date of Patent: May 1, 2012

(54) MONITORING HEART DISEASE USING IMPLANTABLE SENSORS AND SLOPES DETERMINED THEREFROM

(75) Inventors: Yelena Nabutovsky, Mountain View, CA (US); Kyungmoo Ryu, Palmdale, CA (US); Taraneh Ghaffari Farazi, San Jose, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1081 days.

(21) Appl. No.: 11/931,165

(22) Filed: Oct. 31, 2007

(51) Int. Cl.
*A61N 1/37* (2006.01)
*A61N 1/08* (2006.01)

(52) U.S. Cl. .......................... 607/9; 600/508

(58) Field of Classification Search ............ 600/483; 607/9
See application file for complete search history.

(56) References Cited

U.S. PATENT DOCUMENTS

| | | | |
|---|---|---|---|
| 5,743,267 A * | 4/1998 | Nikolic et al. | 600/483 |
| 6,155,267 A | 12/2000 | Nelson | |
| 6,190,324 B1 * | 2/2001 | Kieval et al. | 600/483 |
| 6,882,883 B2 * | 4/2005 | Condie et al. | 607/11 |
| 6,922,587 B2 * | 7/2005 | Weinberg | 607/9 |
| 2002/0198462 A1 | 12/2002 | Begemann | |
| 2004/0172080 A1 | 9/2004 | Stadler | |
| 2004/0267142 A1 | 12/2004 | Paul | |

FOREIGN PATENT DOCUMENTS

| WO | 9321991 A1 | 11/1993 |
|---|---|---|
| WO | 9833554 A1 | 8/1998 |
| WO | 0040143 A1 | 7/2000 |

* cited by examiner

*Primary Examiner* — Carl H Layno
*Assistant Examiner* — Luther Behringer
(74) *Attorney, Agent, or Firm* — Steven M. Mitchell

(57) ABSTRACT

Specific embodiments of the present invention use an implanted sensor, during a period of time, to measure a physiologic property when the patient's heart is not stressed, and when the patient's heart is stressed. A slope is determined, where the slope is indicative of a change in the physiologic property during the period of time. Heart disease is monitored based on a magnitude of the slope. In further embodiments of the present invention, a slope indicative of a change in a physiologic property during a period of time is determined, for each of a plurality of periods of time. Changes in the patient's heart disease are monitored based on changes in the slope.

24 Claims, 5 Drawing Sheets

MONITORING HEART DISEASE USING IMPLANTABLE SENSORS AND SLOPES DETERMINED THEREFROM

CROSS REFERENCE TO RELATED APPLICATIONS

This application relates to commonly invented and commonly assigned U.S. patent application Ser. No. 11/876,560, entitled "Monitoring Heart Disease Using Implantable Sensors", filed on Oct. 22, 2007, which is incorporated herein by reference.

FIELD OF THE INVENTION

Embodiments of the present invention generally relate to using implantable sensors to monitor a patient's heart disease, such as heart failure. Such implantable sensors can be used to measure a physiologic property.

BACKGROUND

Various types of implantable sensors, such as venous oxygen saturation sensors, are becoming more readily available. Such sensors are capable of providing measures of a physiologic property, such as venous oxygen saturation, to an implanted cardiac system, so that such measures can be used as metrics of hemodynamic status, and more specifically, to monitor a patient's heart disease status. A potential problem with such implantable sensors is that they produce a large amount of data, all of which can not be efficiently stored and/or analyzed due to memory and processing constrains of implantable systems. Additionally, where there is an attempt to determine actual values of a physiologic property, such as actual values of venous oxygen saturation, the sensor and/or the sensor measurements must be calibrated from time to time. Otherwise, small inaccuracies and changes in activity and stress levels of the patients can affect the actual values of the physiologic properties that are determined. This can lead to inaccurate monitoring of a patient's heart disease, and the like. It would be beneficial if new and useful methods for using implantable sensors to monitor a patient's heart disease were provided. Preferably, such methods would not require that the implantable sensor (once implanted) be repeatedly calibrated. Additionally, it would be preferable if such methods can provide for a reduction in the amount of data the implantable system stores.

SUMMARY

Embodiments of the present invention relate to systems and methods for monitoring a patient's heart disease, e.g., heart failure, using an implantable sensor that measures a physiologic property. More specifically, many of the embodiments relate to monitoring changes in a patient's heart disease over time. Exemplary physiologic properties include, but are not limited to, venous oxygen saturation (SVO2), left atrial pressure (LAP), cardiogenic impedance (Zc) and transthoracic impedance (Z).

Specific embodiments of the present invention determine a range of a physiologic property, for each of a plurality of periods of time, and monitor changes in the patient's heart disease based on changes in the range. Other embodiments determine a minimum of a physiologic property, for each of a plurality of periods of time, and monitor changes in the patient's heart disease based on changes in the minimum. Still other embodiments determine a maximum of the physiologic property, for each of a plurality of periods of time, and monitor changes in the patient's heart disease based on changes in the maximum. Further embodiments determine a slope indicative of a change in a physiologic property during a period of time, for each of a plurality of periods of time, and monitor changes in the patient's heart disease based on changes in the slope.

In accordance with specific embodiments, during a period of time, an implanted sensor is used to measure a physiologic property when the patient's heart is not stressed, and to measure the physiologic property when the patient's heart is stressed, to thereby determine a range of the physiologic property during the period of time. The above is repeated during further periods of time, to thereby determine a range of the physiologic property during each of the periods of time. Changes in the patient's heart disease are monitored based on how the range of the physiologic property changes over time. This can include determining whether the patient's heart disease worsened, improved or stayed relatively the same, based on how the range of the physiological property changes over time.

The patient's heart can be stressed due to the patient exercising to cause the patient's heart rate and/or activity level to exceed a specified threshold for a specified period of time. Alternatively, the patient's heart can be stressed by pacing the patient's heart to exceed a specified threshold for a specified period of time. The patient's heart can be considered not stressed, e.g., when the patient's heart rate and/or activity level do not exceed a specified threshold for a specified period of time.

In accordance with specific embodiments of the present invention, the implanted sensor can be an implanted venous oxygen saturation sensor, which measures mixed venous oxygen saturation (SVO2). In other words, the physiologic property can be SVO2. In such embodiments, changes in the patient's heart disease can be monitored based on how the range of SVO2 changes over time. This can include interpreting an increase in the range of SVO2 over time as being indicative of worsening of the patient's heart disease, interpreting a decrease in the range of SVO2 over time as being indicative of improvement of the patient's heart disease, and interpreting no substantial change in the range of SVO2 over time as being indicative of the heart disease staying relatively the same.

In other embodiments, the implanted sensor can be, e.g., a left atrial pressure (LAP) sensor, a photoplethysmography (PPG) sensor, a cardiogenic impedance (Zc) or a transthoracic impedance (Z) sensor. Increases and decreases in the range of physiologic properties measured by such implanted sensors can be interpreted in the same way that increases and decreases in the range of SVO2 are interpreted. However, this is not the case for all implanted sensors. For example, the implanted sensor can be a CMES sensor, which measures strength of the contraction of the heart. In this case, a decrease in the range over time can be interpreted as being indicative of worsening of the patient's heart disease and an increase in the range over time can be interpreted as being indicative of improvement of the patient's heart disease. With most sensors, no substantial change in the range can be interpreted as being indicative of the heart disease staying relatively the same.

In accordance with further embodiments of the present invention, during a period of time, an implanted sensor is used to measure a physiologic property, to thereby determine a minimum of the physiologic property during the period of time. This is repeated, during one or more further period of time, to thereby determine the minimum of the physiologic property during each of the one or more further period of time. Changes in the patient's heart disease are monitored based on how the minimum of the physiologic property changes over time.

In accordance with further embodiments of the present invention, during a period of time, an implanted sensor is used to measure a physiologic property, to thereby determine a maximum of the physiologic property during the period of time. This is repeated, during one or more further period of time, to thereby determine the maximum of the physiologic property during each of the one or more further period of time. Changes in the patient's heart disease are monitored based on how the maximum of the physiologic property changes over time.

For certain implantable sensors, such as an SVO2 sensor that measures SVO2, an increase in the minimum (or the maximum) of the physiologic property over time can be interpreted as being indicative of improvement of the patient's heart disease, a decrease in the minimum (or the maximum) of the physiologic property over time can be interpreted as being indicative of worsening of the patient's heart disease. No substantial change in the minimum (or the maximum) of the physiologic property over time can be interpreted as being indicative of the heart disease staying relatively the same.

For other implantable sensors, such left atrial pressure (LAP) sensor that measures left atrial pressure, an increase in the minimum (or the maximum) of the physiologic property over time can be interpreted as being indicative of worsening of the patient's heart disease, a decrease in the minimum (or the maximum) of the physiologic property over time can be interpreted as being indicative of improving of the patient's heart disease. Again, no substantial change in the minimum (or the maximum) of the physiologic property over time can be interpreted as being indicative of the heart disease staying relatively the same.

In accordance with other embodiments of the present invention, during a period of time, an implanted sensor is used to measure a physiologic property when the patient's heart is not stressed, and to measure the physiologic property when the patient's heart is stressed. There is a determination of a slope indicative of a change in the physiologic property during the period of time, and a patient's heart disease can be monitored based on a magnitude of the slope. Additionally, or alternatively, such a slope can be determined for each of a plurality of periods of time, and changes in the heart disease can be monitored based on changes in the magnitude of the slope.

The above can include determining a slope indicative of a change in the physiologic property that occurs in response to the patient's heart changing from not being stressed to being stressed. Additionally, or alternatively, the above can include determining a slope indicative of a change in the physiologic property that occurs in response to the patient's heart changing from being stressed to not being stressed.

Other features and advantages of the invention will appear from the following description in which the preferred embodiments have been set forth in detail, in conjunction with the accompanying drawings and claims.

DETAILED DESCRIPTION

Embodiments of the present invention generally relate to unique ways of using implantable sensors to monitor a patient's heart disease, e.g., heart failure. Such implantable sensors can be used to measure a physiologic property. Exemplary physiologic properties include, but are not limited to, venous oxygen saturation (SVO2), left atrial pressure (LAP), cardiomechanics (CMES), cardiogenic impedance (Zc), and transthoracic impedance (Z). Further, it is noted that the term "physiologic property" as used herein is not meant to encompass heart rate.

Specific embodiments of the present invention determine a range of the physiologic property, for each of a plurality of periods of time, and monitor changes in the patient's heart disease based on changes in the range. Other embodiments determine a minimum of the physiologic property, for each of a plurality of periods of time, and monitor changes in the patient's heart disease based on changes in the minimum. Still other embodiments determine a maximum of the physiologic property, for each of a plurality of periods of time, and monitor changes in the patient's heart disease based on changes in the maximum. Further embodiments determine a slope indicative of a change in the physiologic property, for each of a plurality of periods of time, and monitor changes in the patient's heart disease based on changes in the slope. Each of these embodiments will be described below. Exemplary systems that can be used to implement such methods are also described below.

Range

Figure 1:
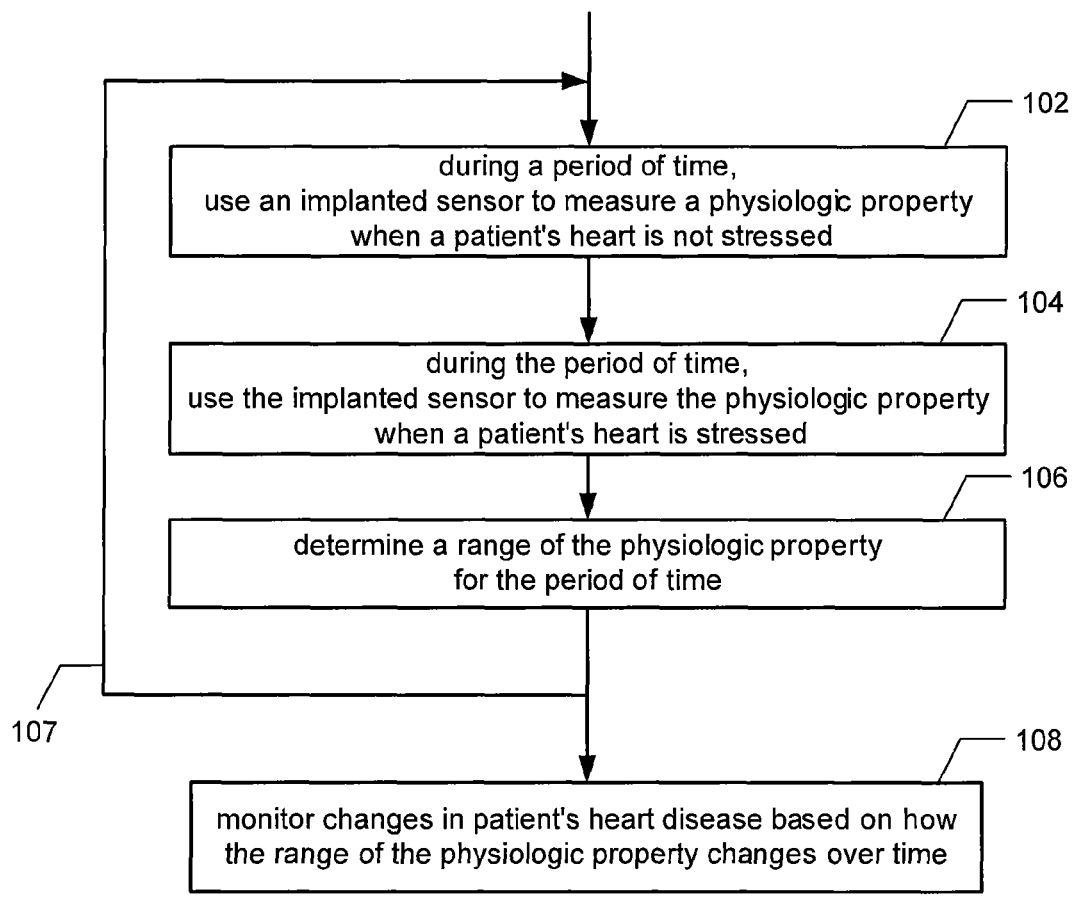
FIG. 1 is a high level flow diagram that is used to explain embodiments of the present invention where the range of a physiologic property, as determined using an implanted sensor, are used for monitoring a patient's heart disease.

The high level flow diagram of FIG. 1 will now be used to explain embodiments of the present invention that monitor changes in the patient's heart disease based on changes in a range of a physiologic property. For the following discussion, it can be assumed that the physiologic property is venous oxygen saturation (SVO2), which is measured using an implanted SVO2 sensor.

Referring to FIG. 1, at step 102, a physiologic property is measured when a patient's heart is not stressed. At step 104, the physiologic property is measured when the patient's heart is stressed. The patient's heart can be stressed, e.g., due to the patient exercising to cause the patient's heart rate and/or activity level to exceed a specified threshold for a specific length of time. For example, a patient can be instructed to perform a 6-minute stress test, where the patient walks on a treadmill or in the hallway for 6-minutes. In an alternative embodiment, the patient's heart can be stressed by pacing the patient's heart to exceed a specified threshold for the specified length of time. The patient's heart can be considered to not be stressed when the patient's heart rate and/or activity level do not exceed a specified threshold for a specified period of time (e.g., 6 minutes).

Preferably steps 102 and 104 occur within a same period of time (e.g., within the same hour, or within the same day). Additionally, data indicative of the physiologic property as measured at steps 102 and 104 can be stored, so that such data can be later retrieved.

At step 106, a range of the physiologic property is determined for the period of time. This can be accomplished by determining the difference between maximum and minimum values of the physiologic property that were obtained at steps 102 and 104. In accordance with certain embodiments, a specified number of highest and lowest data points can be discarded in an attempt to avoid using artifacts. Depending on the physiologic property, maximum values may occur when the patient's heart is not stressed and minimum values may occur when the patient's heart is stressed, or vise versa. For a specific example, a patient's SVO2 will be greater when the patient's heart is not stressed, as compared to when the patient's heart is stressed, because the patient's body will be consuming more oxygen when the patients' heart is stressed. Data indicative of the range determined at step 106 can be stored, so that the data can be later retrieved and/or compared with the range determined for other periods of time. In specific embodiments, the data stored at steps 102 and 104 is overwritten each new period of time with new data, and only the data stored at step 106 is maintained, e.g., so that it can be used for trending, as described below.

As illustrated by arrow 107, steps 102-106 are repeated over time, e.g., once per hour, day, week, etc. This enables changes in the range of the physiologic property to be monitored over time. More specifically, at step 108, changes in the patient's heart disease are monitored based on how the range of the physiologic property changes over time. Step 108 can include determining whether the patient's heart disease worsened, improved or stayed relatively the same, based on how the range of the physiological property changes over time. Since changes in range are used, as opposed to actual values, the need for calibrating the implanted sensor is alleviated. However, the implanted sensor can be calibrated, if desired, e.g., if actual values are used for different reasons.

In specific embodiments of the present invention, the implanted sensor is a venous oxygen saturation sensor, which measures levels of venous oxygen saturation (SVO2). In such embodiments, at steps 102-106, the implanted sensor is used to measure SVO2 when the patient's heart is not stressed, and to measure SVO2 when the patient's heart is stressed, to thereby determine a range of SVO2 during the period of time. These steps are repeated over time, i.e., during one or more further period of time, to thereby determine a range of SVO2 during each of the one or more further period of time. This enables changes in the patient's heart disease to be monitored, at step 108, based on how the range of SVO2 changes over time.

When a patient's heart disease (e.g., heart failure) worsens, the patient's maximum SVO2 (which occurs when the patient's heart is not stressed) should decrease, and the patient's minimum SVO2 (which occurs when the patient's heart is stressed) should also decrease. In such case, the minimum SVO2 should decrease more than the maximum SVO2, which will result in the range of SVO2 increasing with worsening heart disease.

When a patient's heart disease improves, the patient's maximum SVO2 (which occurs when the patient's heart is not stressed) should increase, and the patient's minimum SVO2 (which occurs when the patient's heart is stressed) should also increase. In such case, the minimum SVO2 should increase more than the maximum SVO2, which will result in the range of SVO2 decreasing with improving heart disease.

Based on the above, it can be appreciated that an increase in the range of SVO2 over time can be interpreted as being indicative of worsening of the patient's heart disease. Conversely, a decrease in the range of SVO2 over time can be interpreted as being indicative of improvement of the patient's heart disease. No substantial change in the range of SVO2 over time can be interpreted as being indicative of the heart disease staying relatively the same.

Alternative types of implantable sensors, with which the embodiments of the present invention can be used, include a left atrial pressure (LAP) sensor, a photoplethysmography (PPG) sensor, a cardiogenic impedance (Zc), and a transthoracic impedance (Z) sensor, but are not limited thereto. When using such sensors, it is also believed that an increase in the range over time is indicative of worsening of the patient's heart disease, a decrease in the range over time is indicative of improvement of the patient's heart disease, and no substantial change in the range over time is indicative of the heart disease staying relatively the same. However, with other types of implantable sensors, such as a CMES sensor, it may be the opposite. More specifically, a decrease in the range of CMES over time can be interpreted as being indicative of worsening of the patient's heart disease, and an increase in the range of CMES over time can be interpreted as being indicative of improvement of the patient's heart disease. No substantial change in the range of CMES is indicative of the heart disease staying relatively the same.

A cardiomechanics (CMES) sensor, as the term is used herein, is a sensor that can measure the strength of heart contractions. Such sensors can be implemented as a cardiac wall acceleration or motion sensor, such as those disclosed in U.S. Pat. No. 5,935,158 (Mouchawar et al.) and U.S. Pat. No. 5,628,777 (Moberg et al.). In specific embodiments, a CMES sensor is a piezoelectric sensor, such as those described in PCT Patent Application No. PCT/SE2006/001101, filed Sep. 28, 2006 entitled "Medical Implantable Piezoelectric Sensor and Method for Manufacturing the Same" (Hedberg et al), and PCT Patent Application No. PCT/SE2006/000479, filed Apr. 25, 2006 entitled "A Piezoelectric Sensor, A Method For Manufacturing a Piezoelectric Sensor and a Medical Implantable Lead Comprising Such a Piezoelectric Sensor" (Eriksson et al). Each of these aforementioned patents and applications are incorporated herein by reference. Other types of CMES sensors are also possible.

Based on the above description, one of ordinary skill in the art would understand that by analyzing previously obtained data and/or performing tests, one can determine how to interpret changes in range of other types of physiologic properties measured using other types of implantable sensors. Accordingly, embodiments of the present invention should not be limited to use with the exemplary implantable sensors listed herein.

In the manner just described, a range of a physiologic property can be monitored for the purpose of disease monitoring, including the monitoring of disease progression and/or regression. In specific embodiments, such monitoring can be used for cardiac therapy adjustment. For example, the range of a physiologic property can be used as a measure of hemodynamic function, and thus used in a closed loop for hemodynamic optimization (e.g., A-V delay, VV delay, and/or pacing rate optimization). For a more specific example, monitoring the range of a physiologic property can be used for pacing interval optimization, as well as pacing rate optimization. Exemplary pacing intervals include, but are not limited to, atrio-ventricular (RA-RV) delay, interventricular (RV-LV) delay, interatrial (RA-LA) delay and intraventricular (RV1-RV2 or LV1-LV2) delay. This can include adjusting the pacing interval(s) to attempt to minimize (or maximize) a range of the physiologic property, or maintain the range at a specified level. The specified level can be an optimal level, e.g., as specified by a physician. In specific embodiments, this can include increasing or decreasing specific pacing intervals, or combinations thereof, to attempt to adjust or maintain the range of a physiologic property, depending upon what is desired. In other words, monitoring the range of a physiologic property, determined in accordance with embodiments of the present invention, can be used for closed loop adjustments of pacing parameters, as well as other therapy adjustment.

A Range of a physiologic property can also be compared to one or more threshold, and an alarm and/or therapy can be triggered when the range exceeds (or drops below) a specific threshold. Additionally, or alternatively, changes in a range can be compared to one or more threshold, and an alarm and/or therapy can be triggered and/or adjusted when a change in the range (in the undesired direction) exceeds a specific threshold. In specific embodiments, if an implanted device is appropriately equipped, drug therapy can be delivered and/or adjusted, based on the monitored range. Pacing therapy, which was discussed above, is an example of another type of therapy that can be triggered and/or adjusted based on the monitored range. Such pacing therapy includes cardiac resynchronization therapy, but is not limited thereto. These are just a few examples of the types of responses that can be performed upon detection of a monitored range exceeding (or falling below) a specific threshold. One of ordinary skill in the art would understand from the above description that other responses are also possible, while still being within the spirit and scope of the present invention.

The above described embodiments can be performed autonomously by an implanted device without physician intervention. Alternatively, or additionally, a physician can monitor the range of a physiologic property, and adjust therapy based on the range. For example, a physician may decide to alter a patient's type and/or dosage of medication(s), based on the monitored range of a physiologic property. The physician can also adjust pacing parameters based on the monitored range of a physiologic property.

As was mentioned above, an advantage of monitoring a range of a physiologic property, as opposed to actual values of a physiologic property, is that the need for calibrating the implantable sensor (and/or its measurements) is alleviated. However, as also mentioned above, this does not mean that monitoring the range of a physiologic property is not also useful, even if the implantable sensor (and/or its measurement) are calibrated. Accordingly, embodiments of the present invention cover both situations.

An advantage of monitoring the range of a physiologic property, as opposed to monitoring an average or baseline of the physiologic property, is that more information may be provided by the range. For example, if a patient's average SVO2 is determined for a period of time (e.g., a week), the average SVO2 will be affected by how often the patient's heart is stressed, e.g., by how often the patient exercises, or otherwise exerts themselves. For example, it may be that a patient's heart disease has worsened, which caused the patient to exercise less over the past week. This may result in the patient's average SVO2 increasing, which without more information, would normally be thought of as an improvement in the patient's heart disease.

For a more specific example, presume a patient's heart disease has worsened from one week to the next, i.e., from a first week to a second week. If the patient exerted themselves 10% of the time the first week, but only 2% of the time the second week, the patient's average SVO2 would likely be higher for the second week, even though the patient's heart disease worsened. In contrast, the range of the patient's SVO2 would be lower for the second week, as compared to the first week, which would accurately convey that the patient's heart disease worsened.

The range of a physiologic property can be obtained autonomously by an implanted device, outside a physician's office, e.g., while the patient is going about their normal routine. It's also possible that the patient can be instructed to exercise at least a certain amount of time (e.g., 10 minutes) a specific number of times a week (e.g., 3 times per week), so that the patient's heart is appropriately stressed, enabling the range of the physiologic property to be obtained. It is likely that there will be many periods when patient's heart is not stressed (when the patient is at rest), without instructing the patient to do so. However, it is also possible that the patient may be instructed to rest for a certain length of time, e.g., immediately before and/or after exercising.

In specific embodiments, an activity sensor can be used to determine the patient's level of activity, which can be used to determine whether or not the patient's heart is stressed. For example, it may be that the patient's activity level should be less than a first activity threshold for at least a first amount of time for the patient's heart to be considered not stressed. Similarly, it may be that the patient's activity level should exceed a second activity threshold for at least a second amount of time for the patient's heart to be considered stressed. The first and second activity thresholds can be different, or the same, depending upon the embodiment. The first and second amounts of times can be different, or the same, depending upon the embodiment. Additionally, or alternatively, the patient's heart rate (HR) can be monitored, and the patient's heart can be considered not stressed if a first HR threshold is not exceeded for at least a first amount of time, and the patient's heart can be considered stressed if a second HR threshold is exceeded for at least a second amount of time. The first and second HR thresholds can be different, or the same, depending upon the embodiment. The first and second amounts of times can be different, or the same, depending upon the embodiment.

The range of a physiologic property can alternatively and/or additionally, be obtained within a physician's office, e.g., during the patient's periodic doctor's visit. For example, whenever the patient visits his physician, the physician can instruct the patient to perform the same stress test, e.g., such as a 6-minute walk test or treadmill test. The patient can also be asked to rest for at least a specific length of time. Maximum and minimum values of the physiologic property can, in this manner, be obtained during the visit, and a range of the physiologic property can be determined, and recorded by the physician. This enables the physician to compare the range to previously recorded measures of the range, obtained during previous visits by the patient to the physician. Based on the range, and changes therein, the physician can monitor the patient's heart disease status, as well as adjust medications and/or other therapy, additional details of which were discussed above.

Minimum

As was discussed above, a range of a physiologic property (e.g., SVO2) may change, e.g., because a worsening heart disease causes maximum and minimum values of SVO2 to decrease, but with minimum SVO2 decreasing more than maximum SVO2. In other words, the range of SVO2 increases with worsening heart disease due to the minimum SVO2 decreasing more than the maximum SVO2. Based on this, the inventors of the present invention have realized that it may also be useful and efficient to only monitor minimum SVO2, as well as changes in minimum SVO2, for the purpose of monitoring heart disease. More generally, in accordance with specific embodiments of the present invention, the minimum of a physiologic property can be monitored, as will now be summarized with reference to the flow diagram of FIG. 2.

Figure 2:
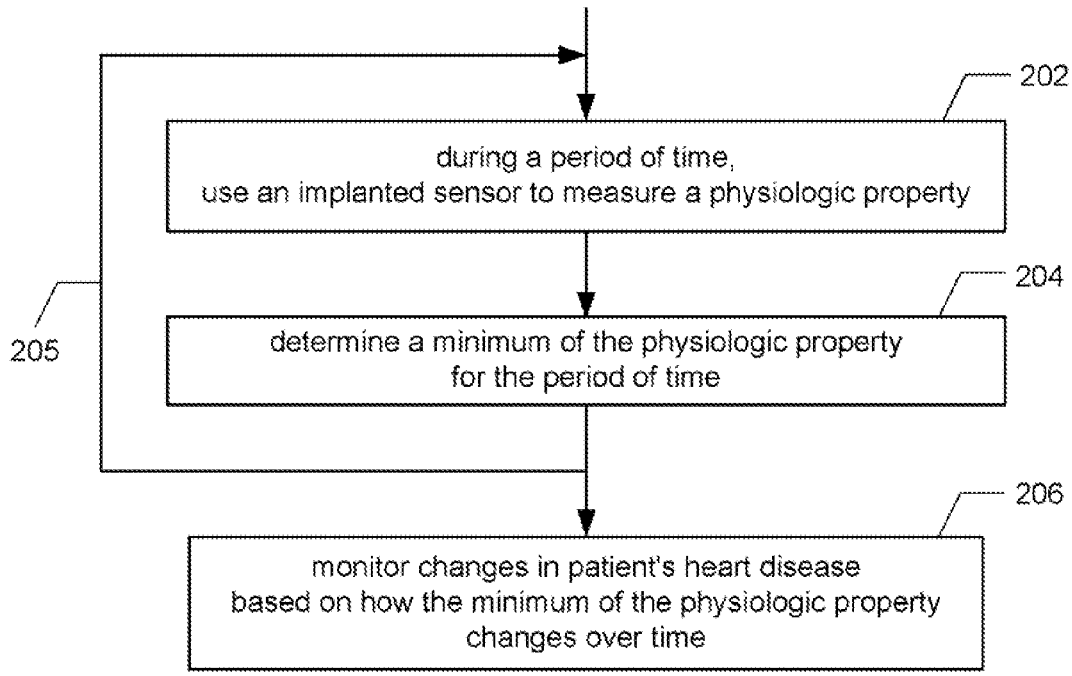
FIG. 2 is a high level flow diagram that is used to explain embodiments of the present invention where the minimum of a physiologic property, as determined using an implanted sensor, are used for monitoring a patient's heart disease.

Referring to FIG. 2, at step 202, an implanted sensor is used to measure a physiologic property during a period of time. At step 204, a minimum of the physiologic property is determined for the period of time. Additionally, data indicative of the minimum of the physiologic property determined at step 204 can be stored, so that such data can be later retrieved. In accordance with certain embodiments, a specified number of lowest data points can be discarded in an attempt to avoid using artifacts. As illustrated by arrow 205, steps 202 and 204 are repeated over time, e.g., once per hour, day, week, etc. This enables changes in the minimum of the physiologic property to be monitored over time. More specifically, at step 206, changes in the patient's heart disease are monitored based on how the minimum of the physiologic property changes over time. Step 206 can include determining whether the patient's heart disease worsened, improved or stayed relatively the same, based on how the minimum of the physiological property changes over time. Since changes in minimum are used, as opposed to actual values, the need for calibrating the implantable sensor is alleviated. However, the implanted sensor can be calibrated, if desired, e.g., if actual values are used for different reasons.

Where the minimum is known to occur while the heart is stressed, it is preferred that the heart is stressed for at least a certain length of time during each period of time referred to as steps 202 and 204. For example, where the physiologic property is SVO2, it is known that minimum SVO2 levels will occur when the patient's heart is stressed. Thus, the patient's heart should be stressed for at least a specific length of time during each period of time referred to at steps 202 and 204. The patient's heart can be stressed in the same manners that were discussed above with reference to step 106 of FIG. 1, including by the patient exercising to cause the patient's heart rate and/or activity level to exceed a specified threshold for a specific length of time, or by pacing the patient's heart to exceed a specified threshold for the specified length of time.

In specific embodiments of the present invention, the implanted sensor is a SVO2 sensor, which measures levels of venous oxygen saturation (SVO2). In such embodiments, at steps 202 and 204, the implanted sensor is used to measure SVO2, to thereby determine the minimum SVO2 during the period of time. These steps are repeated over time, i.e., during one or more further period of time, to thereby determine the minimum SVO2 during each of the one or more further period of time. This enables changes in the patient's heart disease to be monitored, at step 206, based on how the minimum SVO2 changes over time. As was explained above, when a patient's heart disease (e.g., heart failure) worsens, the patient's minimum SVO2 (which occurs when the patient's heart is stressed) should decrease. When a patient's heart disease improves, the patient's minimum SVO2 (which occurs when the patient's heart is stressed) should increase. Thus, it can be appreciated that a decrease in the minimum SVO2 over time can be interpreted as being indicative of worsening of the patient's heart disease. Conversely, an increase in the minimum SVO2 over time can be interpreted as being indicative of improvement of the patient's heart disease. No substantial change in the minimum SVO2 over time can be interpreted as being indicative of the heart disease staying relatively the same.

Alternative types of implantable sensor, with which the embodiments of the present invention can be used, include a cardiogenic impedance (Zc) sensor, a transthoracic impedance (Z) sensor, a photoplethysmography (PPG) sensor and a cardiomechanics (CMES) sensor, but are not limited thereto. When using such sensors, it is also believed that a decrease in the minimum over time is indicative of worsening of the patient's heart disease, an increase in the minimum over time is indicative of improvement of the patient's heart disease, and no substantial change in the minimum over time is indicative of the heart disease staying relative the same. However, with other types of implantable sensors, such as a left atrial pressure (LAP) measuring sensor, it may be the opposite. More specifically, an increase in the minimum LAP over time can be interpreted as being indicative of worsening of the patient's heart disease, and a decrease in the minimum LAP over time can be interpreted as being indicative of improvement of the patient's heart disease. No substantial change in the minimum LAP is indicative of the heart disease staying relatively the same.

Based on the above description, one of ordinary skill in the art would understand that by analyzing existing data and/or performing tests, one can determine how to interpret changes in the minimum of other types of physiologic properties measured using other types of implantable sensors. Accordingly, embodiments of the present invention should not be limited to use with the exemplary implantable sensors listed herein.

As was mentioned above, an advantage of monitoring a minimum of a physiologic property, as opposed to actual values of a physiologic property, is that the need for calibrating the implantable sensor (and/or its measurements) is alleviated. However, as also mentioned above, this does not mean that monitoring the minimum of a physiologic property is not also useful, even if the implantable sensor (and/or its measurements) are calibrated. Accordingly, embodiments of the present invention cover both situations.

There are certain advantages to monitoring a minimum of a physiologic property, as opposed to monitoring an average or baseline of the physiologic property. As mentioned above, if a patient's average SVO2 is determined for a period of time (e.g., a week), the average SVO2 will be affected by how often the patient's heart is stressed, e.g., by how often the patient exercises, or otherwise exerts themselves. For example, presume a patient's heart disease has worsened from one week to the next, i.e., from a first week to a second week. If the patient exerted themselves 10% of the time the first week, but only 2% of the time the second week, the patient's average SVO2 would likely be higher for the second week, even though the patient's heart disease worsened. In contrast, the minimum SVO2 would be lower for the second week, as compared to the first week, which would accurately convey that the patient's heart disease worsened.

In the manner just described, minimums of a physiologic property can be monitored for the purpose of disease monitoring, including the monitoring of disease progression and/or regression. In specific embodiments, such monitoring can be used for cardiac therapy adjustment, examples of which were discussed above in the discussion of FIG. 1, including for hemodynamic optimization (e.g., pacing parameter adjustment), for triggering alarms and/or for triggering therapy and/or changes in therapy. This can include comparing the minimum of a physiologic property, and/or changes in the minimum, to appropriate thresholds.

The minimum of a physiologic property can be obtained autonomously by an implanted device, outside a physician's office, e.g., while the patient is going about their normal routine. It's also possible that the patient can be instructed to exercise at least a certain length of time (e.g., 10 minutes) a specific number of times per week (e.g., 3 times per week), so that the patient's heart is appropriately stressed, enabling the minimum of the physiologic property to be obtained. The minimum of a physiologic property can alternatively, or additionally, be obtained within a physician's office, e.g., during the patient's periodic doctor's visit. For example, whenever the patient visits his physician, the physician can instruct the patient perform the same stress test, e.g., such as a 6-minute walk test or treadmill test. The minimum value of the physiologic property can, in this manner, be obtained during the visit, and the physician can compare the minimum to previously recorded measures of minimum, obtained during previous visits by the patient to the physician's office. Based on the minimum, and changes therein, the physician can monitor the patient's heart disease status, as well as adjust medications and/or other therapy.

In specific embodiments, where the minimum is known to occur while the heart is stressed, an activity sensor can be used to ensure that a patient's activity level is above an activity threshold for at least a specified amount of time, to ensure a patient's heart is sufficiently stressed before minimums of a physiologic property are measured. Additionally, or alternatively, the patient's heart rate (HR) can be monitored, and minimums of a physiologic property may be measured when the patient's HR exceeds a HR threshold for at least a specified amount of time.

In certain embodiments of the present invention, a patient's level of activity and/or HR is monitored, and measures of minimums of a physiologic property are correlated with activity level and/or HR when such measures are stored. This way, if a patient's heart disease condition has worsened to the point that they can no longer reach certain previously reached activity levels and/or HR through exercise, it can be recognized that an increase in the minimum (or in the case of LAP, a decrease in the maximum) may not actually be indicative of an improvement of the condition, but may have occurred because the patient's level of activity and/or HR were unable to reach levels previously reached.

In accordance with specific embodiments, for each period of time a variability of minimums of a physiologic property (or in the case of LAP, the variability of maximums) is determined, for the purpose of monitoring changes in the patient's heart disease condition. It is expected that variability of minimums for most of the physiologic properties mentioned above will increase as a patient's cardiac disease worsens, and that variability of minimums will decrease as a patient's cardiac disease condition improves. For LAP, variability of maximums will increase as a patient's cardiac condition worsens, and decrease as the cardiac condition improves.

Maximum

Figure 3:
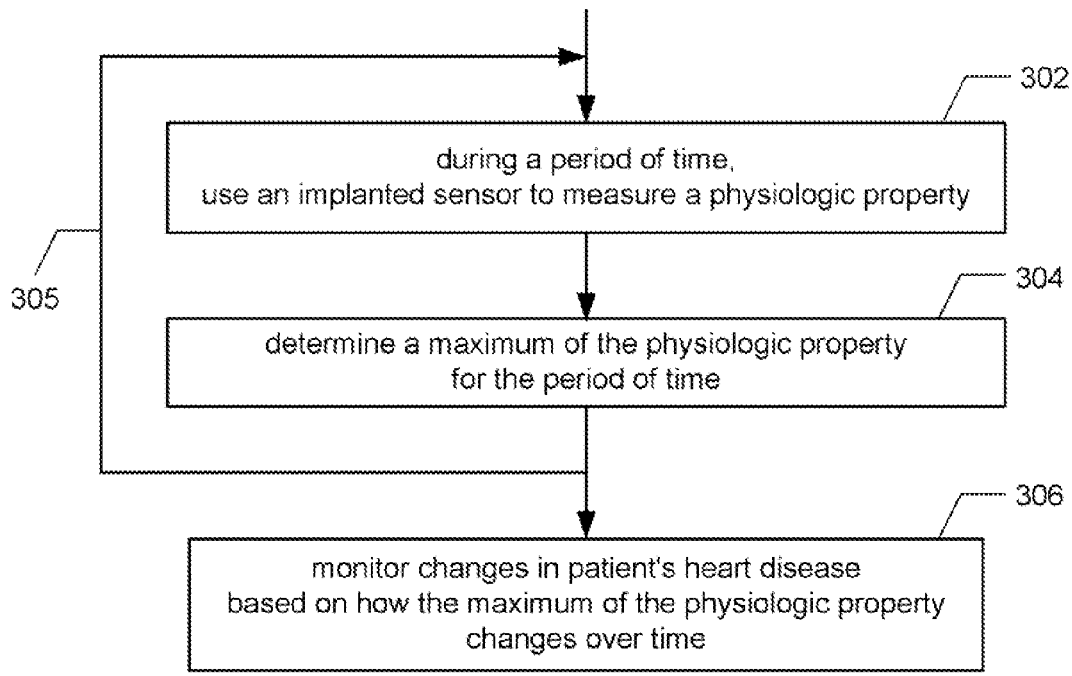
FIG. 3 is a high level flow diagram that is used to explain embodiments of the present invention where the maximum of a physiologic property, as determined using an implanted sensor, are used for monitoring a patient's heart disease.

Instead of monitoring the minimum of a physiologic property, the maximum of a physiologic property can be monitored, as summarized in the flow diagram of FIG. 3. Referring to FIG. 3, at step 302, an implanted sensor is used to measure a physiologic property during a period of time. At step 304, a maximum of the physiologic property is determined for the period of time. In accordance with certain embodiments, a specified number of highest data points can be discarded in an attempt to avoid using artifacts. As illustrated by arrow 305, steps 302 and 304 are repeated over time, e.g., once per hour, day, week, etc. This enables changes in the maximum of the physiologic property to be monitored over time. More specifically, at step 306, changes in the patient's heart disease are monitored based on how the maximums of the physiologic property change over time. Step 306 can include determining whether the patient's heart disease worsened, improved or stayed relatively the same, based on how the maximum of the physiological property changes over time. Since changes in the maximum are used, as opposed to actual values, the need for calibrating the implantable sensor is alleviated. However, the implanted sensor can be calibrated, if desired, e.g., if actual values are used for different reasons.

The maximum of many physiologic properties, such as SVO2, occur when a patient is at rest. It is likely that there will be many periods when patient's heart is not stressed (when the patient is at rest), without instructing the patient to do so. The maximum of other physiologic properties, such as LAP, occur when the patient's heart is stressed. Thus, where an LAP sensor is used, the patient may be instructed to exercise at least a certain length of time (e.g., 10 minutes) a specific number of times per week (e.g., 3 times per week), so that the patient's heart is appropriately stressed, enabling the maximum of the physiologic property to be obtained.

In specific embodiments of the present invention, the implanted sensor is a SVO2 sensor, which measures levels of venous oxygen saturation (SVO2). In such embodiments, at steps 302 and 304, the implanted sensor is used to measure SVO2, to thereby determine a maximum SVO2 during the period of time. These steps are repeated over time, i.e., during one or more further period of time, to thereby determine a maximum of SVO2 during each of the one or more further period of time. This enables changes in the patient's heart disease to be monitored, at step 306, based on how the maximum SVO2 changes over time. As was explained above, when a patient's heart disease (e.g., heart failure) worsens, the patient's maximum SVO2 (which occurs when the patient's heart is not stressed) should decrease. When a patient's heart disease improves, the patient's maximum SVO2 (which occurs when the patient's heart is not stressed) should increase. Thus, it can be appreciated that decreases in the maximum SVO2 over time can be interpreted as being indicative of worsening of the patient's heart disease. Conversely, increases in the maximum SVO2 over time can be interpreted as being indicative of improvement of the patient's heart disease. No substantial change in the maximum SVO2 over time can be interpreted as being indicative of the heart disease staying relatively the same.

Alternative types of implantable sensor, with which the embodiments of the present invention can be used, include a cardiogenic impedance (Zc) sensor, a transthoracic impedance (Z) sensor, a photoplethysmography (PPG) sensor and a cardiomechanic (CMES) sensor, but are not limited thereto. When using such sensors, it is also believed that a decrease in the maximum over time is indicative of worsening of the patient's heart disease, an increase in the maximum over time is indicative of improvement of the patient's heart disease, and no substantial change in the maximum over time is indicative of the heart disease staying relative the same. However, in other types of implantable sensor, such as a LAP measuring sensor, it may be the opposite. More specifically, an increase in the maximum LAP over time can be interpreted as being indicative of worsening of the patient's heart disease, and a decrease in the maximum LAP over time can be interpreted as being indicative of improvement of the patient's heart disease. No substantial change in the maximum LAP is indicative of the heart disease staying relatively the same.

Based on the above description, one of ordinary skill in the art would understand that by analyzing existing data and/or performing tests, one can determine how to interpret changes in the maximum of other types of physiologic properties measured using other types of implantable sensors. Accordingly, embodiments of the present invention should not be limited to use with the exemplary implantable sensors listed herein.

As was mentioned above, an advantage of monitoring the maximum of a physiologic property, as opposed to actual values of a physiologic property, is that the need for calibrating the implantable sensor (and/or its measurements) is alleviated. However, as also mentioned above, this does not mean that monitoring the maximum of a physiologic property is not also useful, even if the implantable sensor (and/or its measurements) are calibrated. Accordingly, embodiments of the present invention cover both situations.

There are certain advantages to monitoring a maximum of a physiologic property, as opposed to monitoring an average or baseline of the physiologic property. As mentioned above, if a patient's average SVO2 is determined for a period of time (e.g., a week), the average SVO2 will be affected by how often the patient's heart is stressed, e.g., by how often the patient exercises, or otherwise exerts themselves. For example, presume a patient's heart disease has worsened from one week to the next, i.e., from a first week to a second week. If the patient exerted themselves 10% of the time the first week, but only 2% of the time the second week, the patient's average SVO2 would likely be higher for the second week, even though the patient's heart disease worsened. In contrast, the maximum SVO2 would be lower for the second week, as compared to the first week, which would accurately convey that the patient's heart disease worsened.

In the manner just described, the maximum of a physiologic property can be monitored for the purpose of disease monitoring, including the monitoring of disease progression and/or regression. In specific embodiments, such monitoring can be used for cardiac therapy adjustment, examples of which were discussed above in the discussion of FIG. 1, including for hemodynamic optimization (e.g., pacing parameter adjustment), for triggering alarms and/or for triggering therapy and/or changes in therapy. This can include comparing the maximum of a physiologic property, and/or changes in the maximum, to appropriate thresholds.

The maximum of a physiologic property can be obtained autonomously by an implanted device, outside a physician's office, e.g., while the patient is going about their normal routine, in similar manners as were discussed above. It's also possible that the patient can be instructed to exercise and/or rest at least a certain length of time a specific number of times per week. In specific embodiments, the maximum of the physiologic property can be obtained during visits to a physician, in similar manners as was described above in the discussion of obtaining the range or the minimum of a physiologic property. Based on the maximum, and changes therein, the physician can monitor the patient's heart disease status, as well as adjust medications and/or other therapy, in similar manners as were explained above.

In specific embodiments, where the maximum is known to occur while the heart is not stressed, an activity sensor can be used to ensure that a patient's activity level is below an activity threshold for at least a specified amount of time, to ensure a patient's heart is sufficiently not stressed before maximums of a physiologic property are measured. Additionally, or alternatively, the patient's heart rate (HR) can be monitored, and maximums of a physiologic property may be measured when the patient's HR does not exceed a HR threshold for at least a specified amount of time.

In certain embodiments of the present invention, a patient's level of activity and/or HR is monitored, and measures of maximums of a physiologic property are correlated with activity level and/or HR when such measures are stored. This way, if a patient did not sufficiently rest during a period, it can be recognized that a decrease in the maximum (or in the case of LAP, an increase in the minimum) may not actually be indicative of a worsening of the condition, but may have occurred because the patient did not sufficiently rest.

Slope

Figure 4:
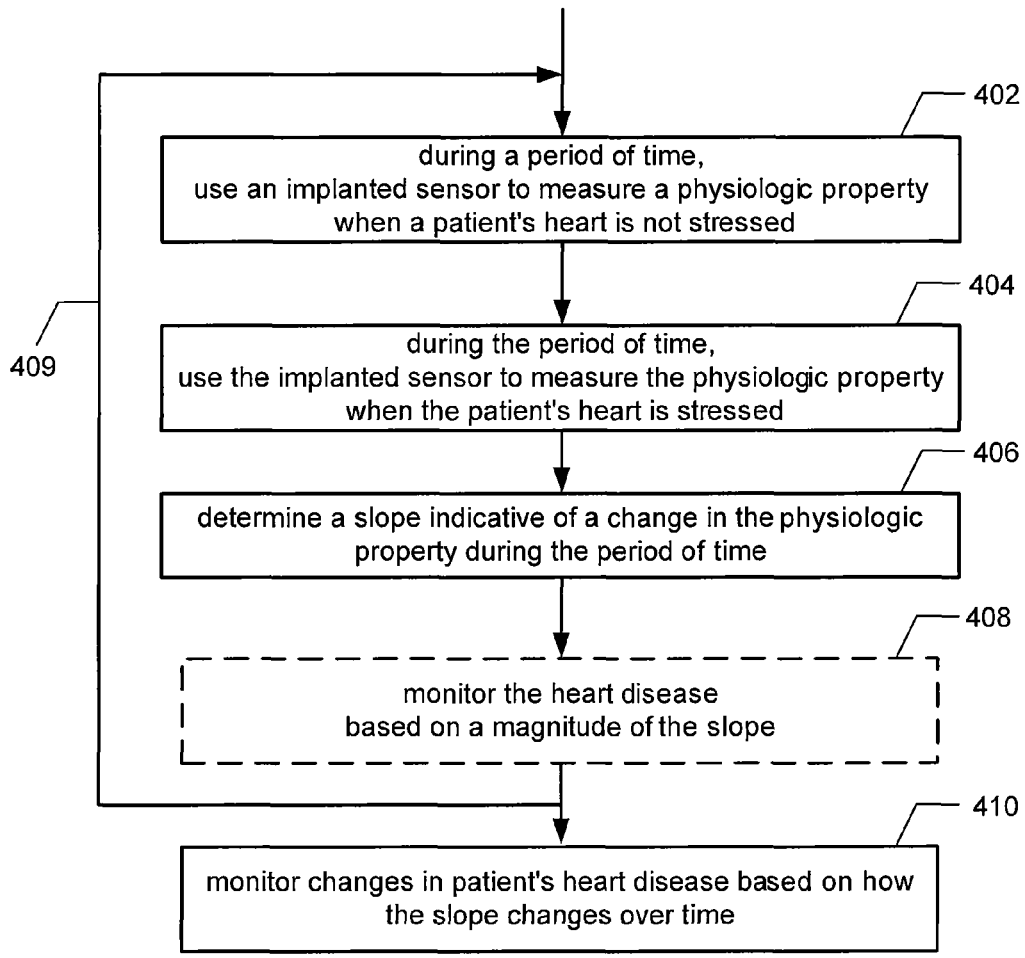
FIG. 4 is a high level flow diagram that is used to explain embodiments of the present invention where slope, indicative of changes in a physiologic property determined using an implanted sensor, are used for monitoring a patient's heart disease.

The high level flow diagram of FIG. 4 will now be used to explain embodiments of the present invention that monitor changes in the patient's heart disease based on a slope indicative of changes in a physiologic property. For the following discussion, it can again be assumed that the physiologic property is venous oxygen saturation (SVO2), which is measured using an implanted SVO2 sensor.

Referring to FIG. 4, at step 402, a physiologic property is measured when a patient's heart is not stressed. At step 404, the physiologic property is measured when the patient's heart is stressed. The patient's heart can be stressed in response to exercise and/or pacing, as was explained above in the discussion of step 104 of FIG. 1. Preferably steps 402 and 404 occur within a same period of time (e.g., within the same hour, or within the same day). Additionally, data indicative of the physiologic property as measured at steps 402 and 404 can be stored, so that such data can be later retrieved.

At step 406, a slope indicative of a change in the physiologic property is determined for the period of time. In specific embodiments, the slope is indicative of a change in SVO2 that occurs in response to the patient's heart changing from not being stressed to being stressed (e.g., if step 402 occurs prior to step 404). Alternatively, or additionally, a slope can be indicative of a change in SVO2 that occurs in response to the patient's heart changing from not being stressed to being stressed (e.g., if step 404 occurs prior to step 402, or more generally, if an instance of step 404 occurs before an instance of step 402). Additionally, data indicative of the slope determined at step 406 can be stored, so that such data can be later retrieved. At step 408, a patient's heart disease, and more specifically an extent thereof, can be monitored based on the magnitude of the slope determined at step 406.

Presuming that the implanted sensor is an SVO2 sensor, steps 402 and 404 can be accomplished by using the implanted sensor to measure SVO2 when the patient's heart is not stressed, and to measure SVO2 when the patient's heart is stressed. At step 406, there is a determination of a slope indicative of a change in SVO2 during the period of time. At step 408, the patient's heart disease is monitored based on a magnitude of the slope.

Presume a patient's SVO2 is at a certain level when the patient's heart is not stressed. In a diseased heart, the drop in SVO2 in response to stressing the patient's heart will be much quicker than in a healthy heart. Thus, the greater the magnitude of the slope indicative of the change in SVO2 in response to a patient's heart going from not being stressed to being stressed, the worse the heart disease status of the patient. In contrast, the lower the magnitude of the slope indicative of the change in SVO2 in response to a patient's heart going from not being stressed to being stressed, the better the heart disease status of the patient.

When a patient's heart changes from being stressed to not being stressed, the patient's SVO2 will increase. The healthier the heart, the quicker the patient's SVO2 will increase. Thus, the greater the magnitude of the slope indicative of the change in SVO2 in response to a patient's heart going from being stressed to not being stressed, the better the heart disease status of the patient. In contrast, the lower the magnitude of the slope indicative of the change in SVO2 in response to a patient's heart going from being stressed to not being stressed, the worse the heart disease status of the patient.

It is noted that the magnitude of the slope can also be referred to in terms of steepness, where the greater the magnitude the greater the steepness, and the lower the magnitude the lower the steepness.

As illustrated by arrow 409, steps 402-408 are repeated over time, e.g., once per hour, day, week, etc. This enables changes in the slopes to be monitored over time. More specifically, at step 410, changes in the patient's heart disease are monitored based on how the slope determined at step 406 changes over time. Step 410 can include determining whether the patient's heart disease worsened, improved or stayed relatively the same, based on how the slope changes over time. Since changes in the slope are used, as opposed to actual values, the need for calibrating the implantable sensor is alleviated. However, the implanted sensor can be calibrated, if desired, e.g., if actual values are used for different reasons.

As mentioned above, where the slope determined at step 406 is indicative of the change in SVO2 in response to a patient's heart going from not being stressed to being stressed, an increase in the magnitude in the slope is indicative of worsening of the patient's heart disease, and a decrease in the magnitude of the slope is indicative of improving of the patient's heart disease. As also mentioned above, where the slope determined at step 406 is indicative of the change in SVO2 in response to the patient's heart going from being stressed to not being stressed, a decrease in the magnitude of the slope is indicative of worsening of the patient's heart disease, and an increase in the magnitude of the slope is indicative of improving of the patient's heart disease. In specific embodiments, both types of slope can be determined at step 406. This enables two types of analysis to be performed at step 410, and the results can be used/provided separately, or combined.

Alternative types of implantable sensors, with which the embodiments of FIG. 4 can be used, include a cardiogenic impedance (Zc) sensor, transthoracic impedance (Z) sensor, left atrial pressure (LAP) sensor, a photoplethysmograph (PPG) sensor and a cardiomechanic (CMES) sensor, but are not limited thereto. When using such sensors, it is believed changes in the magnitudes of the slope can be interpreted in the same manners as were discussed above with regards to an SVO2 sensor. However, it is noted that the slopes for an LAP sensor will be in the opposite directions compared to the other sensors.

In certain embodiments of the present invention, a patient's level of activity and/or HR is monitored, to ensure that during a period of time for which a slope is determined the patient's heart was sufficiently not stressed, and sufficiently stressed. In some embodiments, the determinations of slope are correlated with levels of activity and/or HR. This way, if a patient's heart disease condition has worsened to the point that they can no longer reach certain previously reached activity levels and/or HR through exercise, it can be recognized that this may have been the cause for a change in slope.

Now that various methods of the present invention have been described above, exemplary systems for implementing such embodiments will be described below.

Exemplary Implantable System

Figure 5:
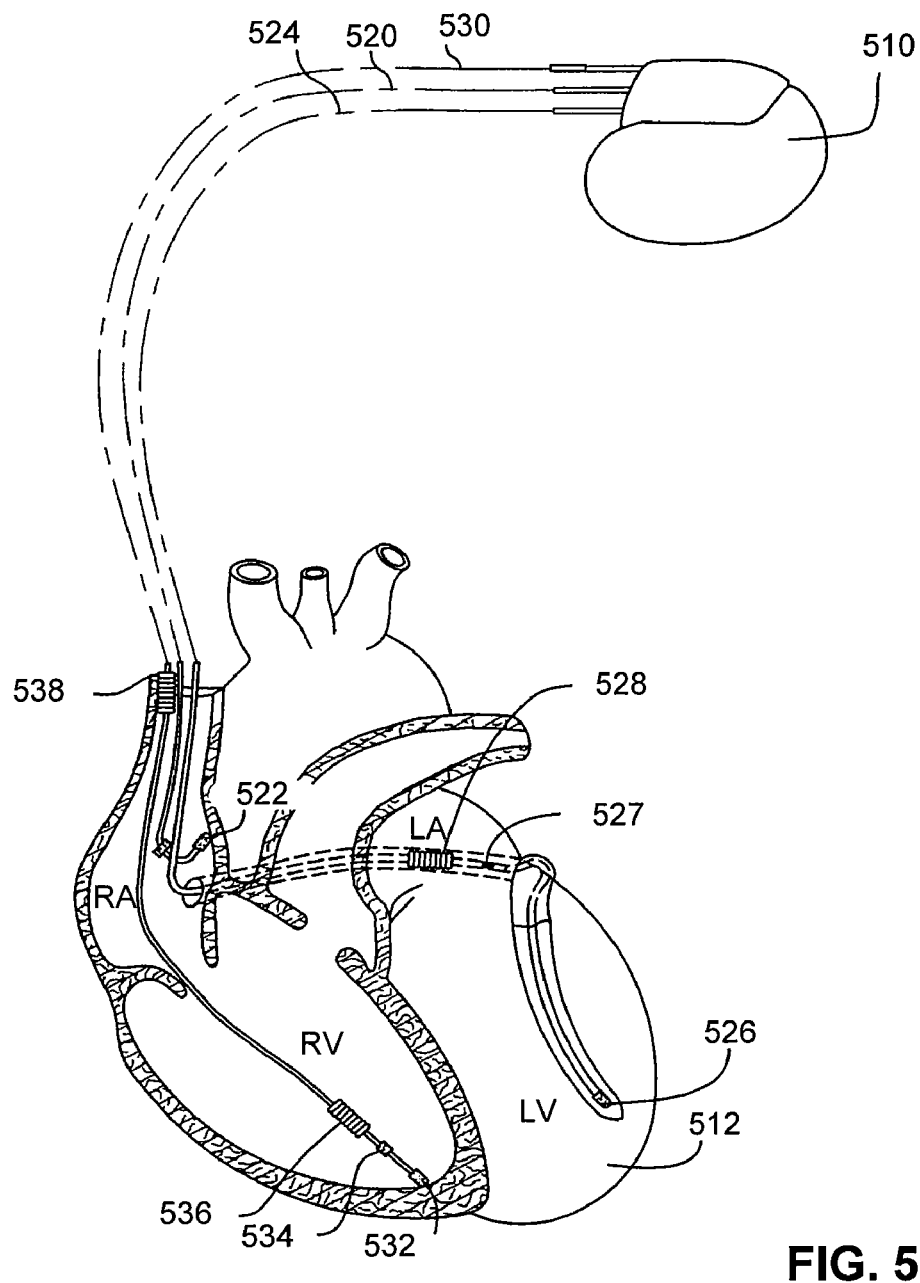
FIG. 5 illustrates an exemplary implantable device which can be used to perform or implement embodiments of the present invention.
Figure 6:
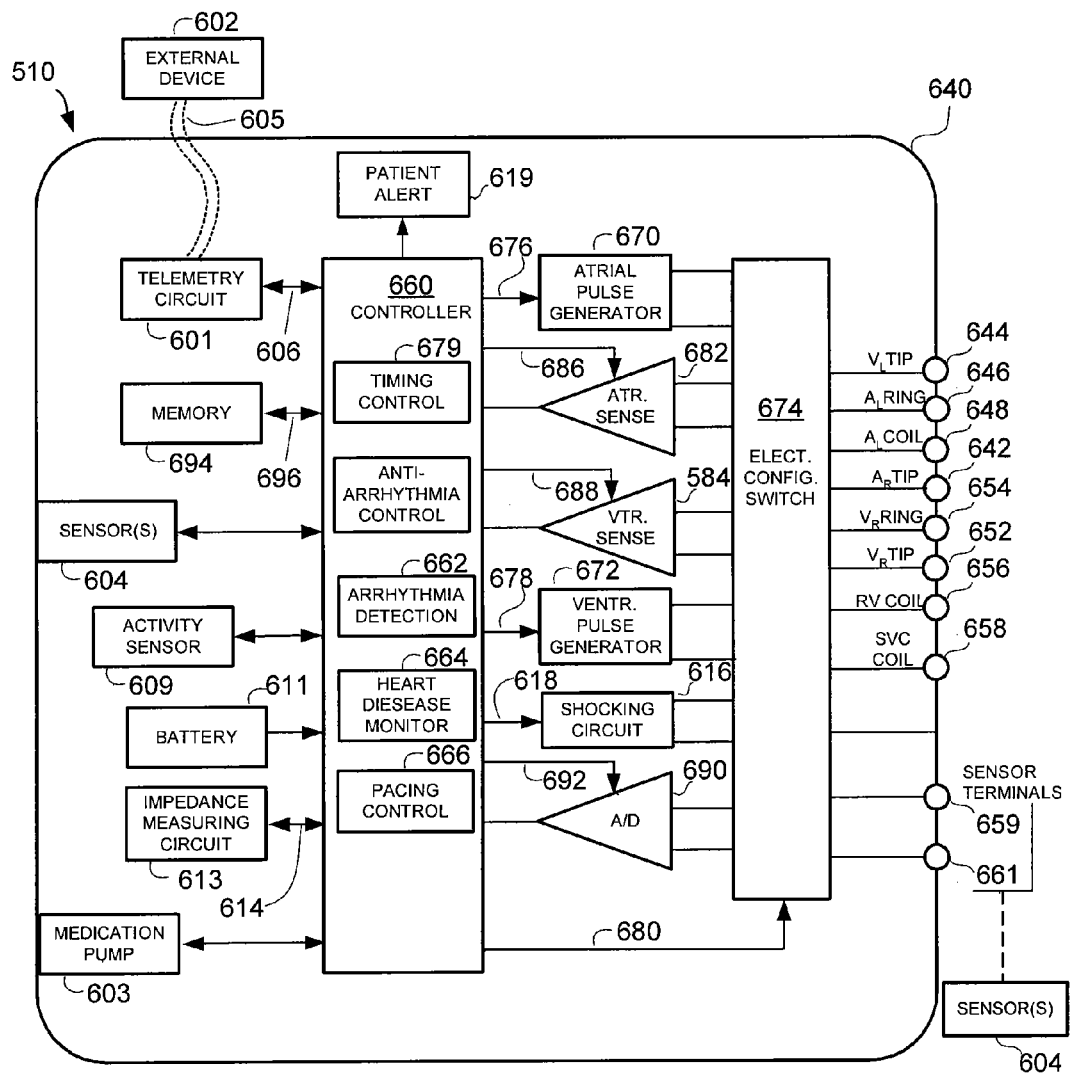
FIG. 6 is a simplified block diagram that illustrates possible components of the implantable device shown in FIG. 5.

FIGS. 5 and 6 will now be used to describe an exemplary implantable system that can be used to monitor a patient's heart disease, in accordance with embodiments of the present invention. Referring to FIG. 5, the implantable system is shown as including an implantable stimulation device 510, which can be a pacing device and/or an implantable cardioverter defibrillator. The device 510 is shown as being in electrical communication with a patient's heart 512 by way of three leads, 520, 524 and 530, which can be suitable for delivering multi-chamber stimulation and shock therapy.

Implantable sensors that measure physiologic properties (represented by blocks 604 in FIG. 6), can be attached to the housing or header of the implantable device 510, or located on or within one of the leads 520, 534 and 530, or a further lead (not shown), that is attached to the implantable device 510. As mentioned above, exemplary implantable sensors include, but are not limited to, an SVO2 sensor, LAP sensor, PPG sensor, CMES sensor, cardiogenic impedance sensor, transthoracic impedance sensor, etc.

Still referring to FIG. 5, to sense atrial cardiac signals and to provide right atrial chamber stimulation therapy, the device 510 is coupled to an implantable right atrial lead 520 having at least an atrial tip electrode 522, which typically is implanted in the patient's right atrial appendage. To sense left atrial and ventricular cardiac signals and to provide left-chamber pacing therapy, the device 510 is coupled to a "coronary sinus" lead 524 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 524 is designed to receive atrial and ventricular cardiac signals and to deliver left ventricular pacing therapy using at least a left ventricular tip electrode 526, left atrial pacing therapy using at least a left atrial ring electrode 527, and shocking therapy using at least a left atrial coil electrode 328.

The device 510 is also shown in electrical communication with the patient's heart 512 by way of an implantable right ventricular lead 530 having, in this embodiment, a right ventricular tip electrode 532, a right ventricular ring electrode 534, a right ventricular (RV) coil electrode 336, and an SVC coil electrode 538. Typically, the right ventricular lead 530 is transvenously inserted into the heart 512 so as to place the right ventricular tip electrode 532 in the right ventricular apex so that the RV coil electrode 536 will be positioned in the right ventricle and the SVC coil electrode 338 will be positioned in the superior vena cava. Accordingly, the right ventricular lead 530 is capable of receiving cardiac signals and delivering stimulation in the form of pacing and shock therapy to the right ventricle.

FIG. 6 will now be used to provides some exemplary details of the components of the implantable devices 510. Referring now to FIG. 6, each of the above implantable devices 510, and alternative versions thereof, can include a microcontroller 660. As is well known in the art, the microcontroller 660 typically includes a microprocessor, or equivalent control circuitry, and can further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design of the microcontroller 660 are not critical to the present invention. Rather, any suitable microcontroller 660 can be used to carry out the functions described herein. The use of microprocessor-based control circuits for performing timing and data analysis functions are well known in the art. In specific embodiments of the present invention, the microcontroller 660 performs some or all of the steps associated with determining the range, minimum and/or maximum of measures of a physiologic propertys, and/or a slope indicative of changes in a physiologic property. Additionally, the microcontroller can determine changes in the range, minimum, maximum and/or slope, and interpret such changes. Additionally, the microcontroller 660 may trigger responses and/or adjust therapy based on such changes, in manners which were described above.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 510 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, where the implantable device is a monitor that does not provide any therapy, it is clear that many of the blocks shown may be eliminated.

The housing 640, shown schematically in FIG. 6, is often referred to as the "can", "case" or "case electrode" and may be programmably selected to act as the return electrode for all "unipolar" modes. The housing 640 may further be used as a return electrode alone or in combination with one or more of the coil electrodes, 528, 536 and 538, for shocking purposes. The housing 640 can further include a connector (not shown) having a plurality of terminals, 642, 644, 646, 648, 652, 654, 656, and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 522.

To achieve left atrial and ventricular sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 526, the left atrial tip electrode 527, and the left atrial coil electrode 528, respectively.

To support right ventricle sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 532, right ventricular ring electrode 534, the RV coil electrode 536, and the SVC coil electrode 538, respectively.

An atrial pulse generator 670 and a ventricular pulse generator 672 generate pacing stimulation pulses for delivery by the right atrial lead 520, the right ventricular lead 530, and/or the coronary sinus lead 524 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators, or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry 679 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, etc.) by selectively closing the appropriate combination of switches (not shown) as is known in the art.

Atrial sensing circuits 682 and ventricular sensing circuits 684 may also be selectively coupled to the right atrial lead 520, coronary sinus lead 524, and the right ventricular lead 530, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers, or shared amplifiers. The switch 674 determines the "sensing polarity" of the cardiac signal by selectively closing the appropriate switches, as is also known in the art. In this way, the clinician may program the sensing polarity independent of the stimulation polarity.

Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables the device 510 to deal effectively with the difficult problem of sensing the low amplitude signal characteristics of atrial or ventricular fibrillation. Such sensing circuits, 682 and 684, can be used to determine cardiac performance values used in the present invention. Alternatively, an automatic sensitivity control circuit may be used to effectively deal with signals of varying amplitude.

The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity, in the appropriate chambers of the heart. The sensing circuits, 682 and 684, in turn, receive control signals over signal lines, 686 and 688, from the microcontroller 660 for purposes of measuring cardiac performance at appropriate times, and for controlling the gain, threshold, polarization charge removal circuitry (not shown), and timing of any blocking circuitry (not shown) coupled to the inputs of the sensing circuits, 682 and 686.

One or more sensor 604 that measures a physiologic property can be located within the housing 640 of the implantable device 510, or connected to the housing 640. Alternatively, one or more sensor 604 can be attached to the implantable device 510 by one or more lead connected to terminals 659 and/or 661 to thereby provide an analog sensor signal to the implantable device. Such a sensor can be attached to a lead or located within a lead. Switch 674 can provide such a signal to an analog-to-digital (ND) converter 690 that converts the signal to a digital format (e.g., into sample data) understood by the microcontroller 660. It is also possible that a dedicated ND converter be provided within the implantable device 610 for the purpose of digitizing a signal received from a sensor 604. If the sensor 604 provides a digital signal to the implantable device 610, then such a signal may be provided directly to the microcontroller 660. It is also possible the one or more implantable sensor 604 can wirelessly communicate with the device 510.

As explained above, the sensor(s) 604 can be a venous oxygen saturation sensor (SVO2) sensor, a left atrial pressure (LAP) sensor, a photoplethysmography (PPG) sensor and/or a cardiomechanic (CMES) sensor. Additionally, or alternatively, the sensor(s) 604 can be a hematocrit sensor and/or a protein sensor, but are not limited thereto. These are just a few exemplary implantable sensors with which embodiments of the present invention may be useful. Embodiments of the present invention can also be used with other sensors that measure physiologic properties other than those just mentioned. Accordingly, sensor(s) 604 can be other types of sensor.

An exemplary implanted SVO2 sensor emits light of two or more wavelengths (e.g., from two or more LEDs) into a blood vessel or heart chamber, and detects reflected light. For estimating oxygen saturation, at least one of the LEDs' primary wavelength is chosen at some point in the electromagnetic spectrum where the absorption of oxyhemoglobin (HbO2) differs from the absorption of reduced hemoglobin (Hb). The one or more other wavelength should be at a different point in the spectrum where, additionally, the absorption differences between Hb and HbO2 are different from those at the first wavelength. Oxygen saturation sensors typically utilize one wavelength in the red part of the visible spectrum near 660 nanometers (nm), and at least one in the near infrared part of the spectrum in the range of 880 nm-940 nm. Photocurrents generated within the photodetector are detected and processed for measuring the ratio of the red to infrared signals. This ratio has been observed to correlate well to oxygen saturation. It is also possible that a single wavelength is used, to not determine a ratio, but rather to measure relative changes in oxygen saturation. The sensor signal associated with such a sensor can be a signal that is indicative of measurements of blood oxygen saturation. Such a sensor signal can be output by the implanted sensor, or a signal produced by a microcontroller or processor that processes raw output signals of the implanted sensor.

In addition to producing measures of blood oxygen saturation, implanted optical sensors can also be used to measure levels of hematocrit, which refers to the percentage of packed red blood cells in a volume of whole blood. Various techniques are known for determining hematocrit based on scattered light. In one technique, a pair of spatially separated photo detectors can be used to detect reflected infra red (IR) light, e.g., of 805 nm. The intensity of the IR light detected by the photo detector that is nearer to the IR light source is referred to as IRnear, and the intensity of the IR light detected by the photo detector farther from the IR light source is referred to as IRfar. As described in article by Bornzin et al., entitled "Measuring Oxygen Saturation and Hematocrit Using a Fiberoptic Catheter", *IEEE/9th Annual Conf of the Eng. & Biol. Soc.* (1997), which is incorporated herein by reference, the ratio: R=IRnear/IRfar is directly related to the level of hematocrit, but independent of oxygen saturation because 805 nm is an isobestic wavelength. Hematocrit can be measured with similar results using a single light detector, and two light sources, where one source is located closer to the light detector than the other (again producing IRnear and IRfar measurements). In another technique, light of about 500 nm and light of about 800 nm can be directed at a blood sample, and an algorithm can be used to calculate hematocrit based on the intensities of detected scattered light.

An implanted PPG sensor similarly includes a light source and a light detector. The PPG sensor can be attached to a housing 640 of the implantable device 510, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, which is incorporated herein by reference. It is also possible that the PPG sensor be integrally part of the implantable device 510. For example, the PPG sensor can be located within the housing 640 of an ICD (or pacemaker) that has a window through which light can be transmitted and detected. In a specific embodiment, the PPG sensor has a titanium frame with a light transparent quartz window that can be welded into a corresponding slot cut in the housing of the ICD. This will insure that the ICD enclosure with the welded PPG sensor will maintain a hermetic condition. Additional details of exemplary implantable PPG sensors are disclosed in U.S. Pat. Nos. 6,409,675 and 6,491,639, both entitled "Extravascular Hemodynamic Sensor" (both Turcott), and U.S. Pat. No. 6,731,967, entitled "Methods and Devices for Vascular Plethysmography via Modulation of Source Intensity" (Turcott), which are incorporated herein by reference.

The implantable device is also shown as including an activity sensor 609, which can detect a patient's level of activity. The sensor 609 can be, e.g., a DC-coupled 3-dimensional accelerometer as described in U.S. Pat. No. 6,658,292 (Kroll et al), a multi-axis DC accelerometer as described in U.S. Pat. No. 6,466,821 (Pianca et al), or an external field sensor as described in U.S. Pat. No. 6,625,493 (Kroll et al), each of which are incorporated herein by reference. Such sensors can detect a level of patient activity, and thus whether it is likely that a patient's heart is stressed or not. More specifically, if a detected level of activity exceeds a certain threshold, the patient's heart can be considered to be stressed. In contrast, the patient's heart can be considered to not be stressed when the detected level of activity level falls below a threshold. A common threshold can be used, or there can be a first activity threshold that must be exceeded for the patient's heart to be considered stressed, and a second activity threshold which must not be exceeded for the patient's heart to be considered not stressed.

For arrhythmia detection, the device 510 includes an arrhythmia detector 662 that utilizes the atrial and ventricular sensing circuits, 682 and 684, to sense cardiac signals to determine whether a rhythm is physiologic or pathologic. The timing intervals between sensed events (e.g., P-waves, R-waves, and depolarization signals associated with fibrillation) can be classified by the microcontroller 660 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 662 can be implemented within the microcontroller 660, as shown in FIG. 6. Thus, this detector 662 can be implemented by software, firmware, or combinations thereof. It is also possible that all, or portions, of the arrhythmia detector 662 can be implemented using hardware. Further, it is also possible that all, or portions, of the ischemia detector 662 can be implemented separate from the microcontroller 660.

In accordance with embodiments of the present invention, the implantable device 510 includes heart disease monitor 664, which can monitor levels and changes of a patient's heart disease, including worsening (progression) and improving (regression) of the heart disease. Such a heart disease can be heart failure, but need not be. The heart disease monitor 664 can be implemented within the microcontroller 660, as shown in FIG. 6, and can the be implemented by software, firmware, or combinations thereof. It is also possible that all, or portions, of the monitor 664 to be implemented using hardware. Further, it is also possible that all, or portions, of the monitor 664 to be implemented separate from the microcontroller 660. The heart disease monitor 664 can be used in a closed loop control system to provide an assessment of hemodynamic status during pacing parameter adjustments, and/or as an assessment of hemodynamic status during a detected arrhythmia. Such measures of hemodynamic status can be used when determining which anti-arrhythmia therapy options are appropriate.

The implantable device 510 can also include a pacing controller 666, which can adjust a pacing rate and/or pacing intervals based on measures a physiologic property, changes in a physiologic property, status of a patient's heart disease, and/or changes in the patient's heart disease, determined in the manners discussed above. The pacing controller 666 can be implemented within the microcontroller 660, as shown in FIG. 6. Thus, the pacing controller 666 can be implemented by software, firmware, or combinations thereof. It is also possible that all, or portions, of the pacing controller 666 can be implemented using hardware. Further, it is also possible that all, or portions, of the pacing controller 666 can be implemented separate from the microcontroller 660.

The implantable device can also include a medication pump 603, which can deliver medication to a patient if the patient's heart disease condition and/or change therein, exceeds or falls below specific thresholds. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 6, cardiac signals are also applied to the inputs of an analog-to-digital (ND) data acquisition system 690. The data acquisition system 690 is configured to acquire IEGM and/or ECG signals, convert the raw analog data into a digital signal, and store the digital signals for later processing and/or telemetric transmission to an external device 602. The data acquisition system 690 can be coupled to the right atrial lead 320, the coronary sinus lead 524, and the right ventricular lead 530 through the switch 674 to sample cardiac signals across any pair of desired electrodes.

The data acquisition system 690 can be coupled to the microcontroller 660, or other detection circuitry, for detecting an evoked response from the heart 412 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 660 detects a depolarization signal during a window following a stimulation pulse, the presence of which indicates that capture has occurred. The microcontroller 660 enables capture detection by triggering the ventricular pulse generator 672 to generate a stimulation pulse, starting a capture detection window using the timing control circuitry 679 within the microcontroller 660, and enabling the data acquisition system 690 via control signal 692 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 660 is further coupled to the memory 694 by a suitable data/address bus 696, wherein the programmable operating parameters used by the microcontroller 660 are stored and modified, as required, in order to customize the operation of the implantable device 510 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy.

The memory 694 can also store data indicative of measures of one or more physiologic property, the range of one or more physiologic property, the minimum of one or more physiologic property, the maximum of one or more physiologic property and/or the slope indicative of changes in one or more physiologic property. In order to significantly reduce the amount of data that an implantable device stores, in specific embodiments, rather than storing data indicative of all the actual measures of a physiologic property determined during a period of time (e.g., an hour, day, week, etc), only data indicative of the range of the measures for that period of time is stored. Alternatively, only data indicative of the minimum of the measures for that period of time is stored. In other embodiments, only data indicative of the maximum of the measures for that period of time is stored. In a further embodiment, only data indicative of the slope indicative of a change of the measures (in response to a change from when the patient's heart is not stressed, to being stressed, and/or vise versa) is stored. Combinations of data indicative of the range, minimum, maximum and slope can also be stored. It's also possible that measures of a physiologic property for a most recent period of time are stored, and then once the range, minimum, maximum and/or slope is determined based on such measures, the range, minimum, maximum and/or slope is stored, and the stored measures of the physiologic property are written over during a further period of time. This can be done for each of a plurality of periods of time, to reduce the amount of data that need be stored. The memory 694 can also store information related to the patient's heart disease status, as determined in accordance with embodiments of the present invention.

A telemetry circuit 601 can be used to wirelessly transmit such data to an external device 602, such as a programmer, monitor, transtelephonic transceiver, or a diagnostic system analyzer. The telemetry circuit can send data indicative of the range, minimum, maximum and/or slope of a physiologic property, and/or a change in the same, as determined in accordance with embodiments of the present invention, to the external device 602. Alternatively, the telemetry circuit 601 can transmit data indicative measures of the physiologic property, and the external device 602 can determine the range, minimum, maximum, slope, and/or changes in the same, based on the measures. Accordingly, it can be the external device 602 that implements the a heart disease monitor, using measures provided to it by the implantable device 510.

The operating parameters of the implantable device 510 may be non-invasively programmed into the memory 694 through the telemetry circuit 601 in telemetric communication with an external device 602. The telemetry circuit 601 can be activated by the microcontroller 660 by a control signal 606. The telemetry circuit 601 advantageously allows intracardiac electrograms and status information relating to the operation of the device 510 (as contained in the microcontroller 660 or memory 694) to be sent to the external device 602 through an established communication link 605.

For examples of telemetry devices, see U.S. Pat. No. 4,809,697, entitled "Interactive Programming and Diagnostic System for use with Implantable Pacemaker" (Causey, Ill. et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 510 additionally includes a battery 611 which provides operating power to all of the circuits shown in FIG. 6. If the implantable device 510 also employs shocking therapy, the battery 611 should be capable of operating at low current drains for long periods of time, and then be capable of providing high-current pulses (for capacitor charging) when the patient requires a shock pulse. The battery 611 should also have a predictable discharge characteristic so that elective replacement time can be detected.

The implantable device 510 can also include a magnet detection circuitry (not shown), coupled to the microcontroller 660. It is the purpose of the magnet detection circuitry to detect when a magnet is placed over the implantable device 510, which magnet may be used by a clinician to perform various test functions of the implantable device 510 and/or to signal the microcontroller 660 that the external programmer 602 is in place to receive or transmit data to the microcontroller 660 through the telemetry circuits 601.

As further shown in FIG. 6, the device 510 is also shown as having an impedance measuring circuit 613 which is enabled by the microcontroller 660 via a control signal 614. The known uses for an impedance measuring circuit 613 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 613 is advantageously coupled to the switch 674 so that any desired electrode may be used. The impedance measuring circuit 613 is not critical to the present invention and is shown only for completeness.

In the case where the implantable device 510 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 660 further controls a shocking circuit 616 by way of a control signal 618. The shocking circuit 616 generates shocking pulses of low (up to 0.5 Joules), moderate (0.5-10 Joules), or high energy (11 to 40 Joules), as controlled by the microcontroller 660. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 640 may act as an active electrode in combination with the RV electrode 336, or as part of a split electrical vector using the SVC coil electrode 338 or the left atrial coil electrode 328 (i.e., using the RV electrode as a common electrode).

The above described implantable device 510 was described as an exemplary pacing device. One or ordinary skill in the art would understand that embodiments of the present invention can be used with alternative types of implantable devices. Accordingly, embodiments of the present invention should not be limited to use only with the above described device. For example, the implantable device 510 can be a simple monitoring device that does not provide any type of cardiac stimulation.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 1-4. Further, it is possible to change the order of some of the steps shown in FIGS. 1-4, without substantially changing the overall events and results. For another example, it is possible to change the boundaries of some of the blocks shown in FIG. 6.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring a patient's heart disease, comprising:
  (a) during a period of time, using an implanted sensor to measure a physiologic property when the patient's heart is not stressed, and to measure the physiologic property when the patient's heart is stressed by pacing the patient's heart to exceed a specified threshold for a specified length of time;
  (b) determining a slope indicative of a change in the physiologic property that occurs in response to the patient's heart changing from not being stressed to being stressed, or vice versa, during the period of time; and
  (c) monitoring an extent of the heart disease based on a magnitude of the slope;
  wherein the physiologic property is selected from the group consisting of venous oxygen saturation (SVO2), left atrial pressure (LAP), cardiomechanics (CMES), cardiogenic impedance (Zc) and transthoracic impedance (Z).

2. The method of claim 1, wherein the patient's heart is not stressed when a level of activity determined using an activity sensor and/or a measure of heart rate do not exceed a corresponding specified threshold for a corresponding specified period of time.

3. The method of claim 1, wherein:
step (b) includes determining a slope indicative of a change in the physiologic property that occurs in response to the patient's heart changing from not being stressed to being stressed.

4. The method of claim 1, wherein:
step (b) includes determining a slope indicative of a change in the physiologic property that occurs in response to the patient's heart changing from being stressed to not being stressed.

5. The method of claim 1, wherein:
step (b) includes
   (b.1) determining a first slope indicative of a change in the physiologic property that occurs in response to the patient's heart changing from not being stressed to being stressed; and
   (b.2) determining a second slope indicative of a change in the physiologic property that occurs in response to the patient's heart changing from being stressed to not being stressed; and
step (c) includes monitoring an extent of the heart disease based on the magnitude of the first slope and the magnitude of the second slope.

6. The method of claim 1, wherein:
steps (a) and (b) are repeated during one or more further period of time, to thereby determine a slope indicative of a change in the physiologic property during each of the one or more further period of time; and
step (c) includes monitoring changes in the heart disease, based on changes in the magnitude of the slope.

7. The method of claim 6, wherein step (c) includes determining whether the heart disease progressed, regressed or stayed relatively the same, based on how the magnitude of the slope changes over time.

8. A system for monitoring a patient's heart disease, comprising:
an implantable sensor to measure a physiologic property when the patient's heart is not stressed, and to measure the physiologic property when the patient's heart is stressed by pacing the patient's heart to exceed a specified threshold for a specified length of time; and
a heart disease monitor to determine a slope indicative of a change in the physiologic property that occurs in response to the patient's heart changing from not being stressed to being stressed, or vice versa, during the period of time; and
wherein the monitor monitors the heart disease based on a magnitude of the slope;
wherein the physiologic property is selected from the group consisting of venous oxygen saturation (SVO2), left atrial pressure (LAP), cardiomechanics (CMES), cardiogenic impedance (Zc) and transthoracic impedance (Z).

9. The system of claim 8, further comprising:
an implantable activity sensor;
wherein the patient's heart is not stressed when a level of activity determined using the activity sensor and/or a measure of heart rate do not exceed a corresponding specified threshold for a corresponding specified period of time.

10. The system of claim 8, wherein:
the monitor determines a slope indicative of a change in the physiologic property that occurs in response to the patient's heart changing from not being stressed to being stressed.

11. The system of claim 10, wherein:
the monitor determines a second slope indicative of a change in the physiologic property that occurs in response to the patient's heart changing from being stressed to not being stressed.

12. The system of claim 8, wherein:
the monitor determines a slope indicative of a change in the physiologic property that occurs in response to the patient's heart changing from being stressed to not being stressed; and
the monitor monitors the heart disease based on the magnitude of the slope.

13. The system of claim 8, wherein the monitor determines changes in the patient's heart disease based on how the slope changes over time.

14. A method for monitoring a patient's heart disease, comprising:
(a) during a period of time, using an implanted sensor to measure a physiologic property when the patient's heart is not stressed, and to measure the physiologic property when the patient's heart is stressed by pacing the patient's heart to exceed a specified threshold for a specified length of time, to thereby determine a slope indicative of a change in the physiologic property that occurs in response to the patient's heart changing from not being stressed to being stressed, or vice versa, during the period of time; and
(b) repeating step (a) during one or more further period of time, to thereby determine a slope indicative of a change in the physiologic property during each of the one or more further period of time; and
(c) monitoring changes in the patient's heart disease based on how the slope changes over time;
wherein the physiologic property is selected from the group consisting of venous oxygen saturation (SVO2), left atrial pressure (LAP), cardiomechanics (CMES), cardiogenic impedance (Zc) and transthoracic impedance (Z).

15. The method of claim 14, wherein:
step (a) includes determining a slope indicative of a change in the physiologic property that occurs in response to the patient's heart changing from not being stressed to being stressed; and
step (c) includes monitoring changes in the patient's heart disease based on how the magnitude of the slope changes over time.

16. The method of claim 14, wherein:
step (a) includes determining a slope indicative of a change in the physiologic property that occurs in response to the patient's heart changing from being stressed to not being stressed; and
step (c) includes monitoring changes in the patient's heart disease based on how the magnitude of the slope changes over time.

17. The method of claim 14, wherein:
step (a) includes
   determining a first slope indicative of a change in the physiologic property that occurs in response to the patient's heart changing from not being stressed to being stressed; and
   determining a second slope indicative of a change in the physiologic property that occurs in response to the patient's heart changing from being stressed to not being stressed; and
step (c) includes monitoring changes in the patient's heart disease based on how the magnitude of the first slope and the magnitude of the second slope changes over time.

18. The method of claim 14, wherein:
the implantable sensor comprises an implanted venous oxygen saturation sensor;
the physiologic property comprises venous oxygen saturation (SVO2);
for each period of time step (a) includes determining a slope indicative of a change in SVO2 that occurs in response to the patient's heart changing from not being stressed to being stressed; and
step (c) includes
interpreting an increase in the magnitude of the slope over time as being indicative of worsening of the heart disease;
interpreting a decrease in the magnitude of the slope over time as being indicative of improvement of the heart disease; and
interpreting no substantial change in the magnitude of the slope over time as being indicative of the heart disease staying relative the same.

19. The method of claim 14, wherein:
the implanted sensor comprises an implanted venous oxygen saturation sensor;
the physiologic property comprises venous oxygen saturation (SVO2);
for each period of time step (a) includes determining a slope indicative of a change in SVO2 that occurs in response to the patient's heart changing from being stressed to not being stressed; and
step (c) includes
interpreting a decrease in the magnitude of the slope over time as being indicative of worsening of the heart disease;
interpreting an increase in the magnitude of the slope over time as being indicative of improvement of the heart disease; and
interpreting no substantial change in the magnitude of the slope over time as being indicative of the heart disease staying relative the same.

20. A system for monitoring a patient's heart disease, comprising:
at least one pulse generator to generate pacing pulses for pacing the patient's heart;
an implanted sensor to measure of physiologic property; and
a heart disease monitor to monitor the physiologic property when the patient's heart is not stressed, and to monitor the physiologic property when the patient's heart is stressed by pacing the patient's heart to exceed a specified threshold for a specified length of time, to thereby determine a slope indicative of a change in the physiologic property that occurs in response to the patient's heart changing from not being stressed to being stressed, or vice versa, for each of a plurality of periods of time;
wherein the monitor monitors changes in the patient's heart disease based on how a magnitude of the slope changes over time;
wherein the physiologic property is selected from the group consisting of venous oxygen saturation (SVO2), left atrial pressure (LAP), cardiomechanics (CMES), cardiogenic impedance (Zc) and transthoracic impedance (Z).

21. The system of claim 20, wherein the slope is indicative of a change in the physiologic property that occurs in response to the patient's heart changing from not being stressed to being stressed.

22. The system of claim 21, wherein the slope is indicative of a change in the physiologic property that occurs in response to the patient's heart changing from being stressed to not being stressed.

23. The system of claim 21, wherein the monitor:
determines a first slope indicative of a change in the physiologic property that occurs in response to the patient's heart changing from not being stressed to being stressed;
determines a second slope indicative of a change in the physiologic property that occurs in response to the patient's heart changing from being stressed to not being stressed; and
monitors changes in the patient's heart disease based on the first and second slopes.

24. The system of claim 21, further comprising:
an implantable activity sensor;
wherein the patient's heart is not stressed when a level of activity determined using the activity sensor and/or a measure of heart rate do not exceed a corresponding specified threshold for a corresponding specified period of time.

* * * * *